(12) United States Patent
Lueder et al.

(10) Patent No.: US 6,340,665 B1
(45) Date of Patent: Jan. 22, 2002

(54) METHOD FOR PRODUCING NEUTRAL SUGAR SURFACTANT GRANULATES

(75) Inventors: Thomas Lueder, Langenfeld; Konstantinos Scholinakis, Monheim; Bernhard Gutsche, Hilden; Hermann Hensen, Haan; Werner Seipel, Hilden, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/380,916

(22) PCT Filed: Mar. 3, 1998

(86) PCT No.: PCT/EP98/01178

§ 371 Date: Dec. 14, 1999

§ 102(e) Date: Dec. 14, 1999

(87) PCT Pub. No.: WO98/40460

PCT Pub. Date: Sep. 17, 1998

(30) Foreign Application Priority Data

Mar. 12, 1997 (DE) .......................... 197 10 153

(51) Int. Cl.$^7$ .............................. C11D 1/00; C08B 37/00
(52) U.S. Cl. ..................... 510/470; 536/18.7; 536/22.1; 536/4.1; 536/120; 536/124; 536/127
(58) Field of Search .................. 510/470; 536/18.7, 536/22.1, 4.1, 120, 124, 127

(56) References Cited

U.S. PATENT DOCUMENTS

| | | | |
|---|---|---|---|
| 1,985,424 A | 12/1934 | Piggott | 260/124 |
| 2,016,962 A | 10/1935 | Flint et al. | 260/127 |
| 2,703,798 A | 3/1955 | Schwartz | 260/211 |
| 5,374,716 A | 12/1994 | Biermann et al. | 536/18.6 |
| 5,401,839 A * | 3/1995 | Au et al. | 536/18.7 |
| 5,536,431 A | 7/1996 | Carduck et al. | 510/444 |
| 5,576,425 A | 11/1996 | Hill et al. | 536/18.6 |
| 5,844,103 A * | 12/1998 | Au et al. | 536/17.2 |

FOREIGN PATENT DOCUMENTS

| | | |
|---|---|---|
| DE | 41 02 745 | 8/1992 |
| DE | 41 39 551 | 6/1993 |
| DE | 42 09 339 | 9/1993 |
| DE | 195 20 105 | 3/1996 |
| DE | 195 34 371 | 2/1997 |
| EP | 0 301 298 | 2/1989 |
| WO | WO90/03977 | 4/1990 |
| WO | WO92/06984 | 4/1992 |
| WO | WO95/14519 | 6/1995 |

OTHER PUBLICATIONS

Tens. Surf. Det. 25, vol. 8, (1988).

* cited by examiner

Primary Examiner—Ralph Gitomer
Assistant Examiner—Devesh Khare
(74) Attorney, Agent, or Firm—John E. Drach; Glenn E. J. Murphy; Steven J. Trzaska

(57) ABSTRACT

A process for making neutral sugar surfactant granules involving: (a) providing a water-containing alkaline sugar surfactant selected from the group consisting of an alkyl oligoglycoside, an alkenyl oligoglycoside, a fatty acid-N-alkyl polyhydroxyalkylamide, and mixtures thereof; (b) providing a thin-layer evaporator or dryer having rotating internals; (c) neutralizing the water-containing alkaline sugar surfactant to a pH of from 6.8 to 7.5 to form a neutralized water-containing sugar surfactant; (d) introducing the neutralized water-containing alkaline sugar surfactant into the thin-layer evaporator or dryer; and (e) drying the water-containing alkaline sugar surfactant in the thin-layer evaporator or dryer until it has a residual water content below 2% by weight.

11 Claims, No Drawings

METHOD FOR PRODUCING NEUTRAL SUGAR SURFACTANT GRANULATES

BACKGROUND OF THE INVENTION

This invention relates to a process for the simultaneous drying and granulation of water-containing, alkaline sugar surfactant pastes in a thin layer evaporator/dryer.

Sugar surfactants, for example alkyl oligoglucosides or fatty acid-N-alkyl glucamides, are distinguished by excellent detergent properties and high ecotoxicological compatibility. For this reason, these classes of non-ionic surfactants are acquiring increasing significance. Although, hitherto, they have generally been used in liquid formulations, for example dishwashing detergents or hair shampoos, there is now also a market need for solid, water-free formulations which may even be incorporated, for example, in powder-form detergents or syndet soaps.

On an industrial scale, liquid surfactant formulations are generally dried by conventional spray drying, in which the water-containing surfactant paste is sprayed in the form of fine droplets at the head of a tower, the droplets encountering hot drying gases flowing in countercurrent. Unfortunately, this technology cannot readily be applied to sugar surfactant pastes because the temperatures required for drying are above the caramelization temperature, i.e. the decomposition temperature, of the sugar surfactants. The conventional drying of sugar surfactant pastes results in the formation of carbonized products, in addition to which caking occurs on the walls of the spray drying tower so that they have to be cleaned at considerable expense at short intervals.

Attempts have been made in the past to overcome this problem. For example, German patent application DE-A1 41 02 745 (Henkel) describes a process in which a small quantity of 1 to 5% by weight of alkyl glucosides is added to fatty alcohol pastes which are then conventionally spray dried. Unfortunately, the process can only be carried out in the presence of a large quantity of inorganic salts. According to German patent application DE-A1 41 39 551 (Henkel), pastes of alkyl sulfates and alkyl glucosides which may contain at most only 50% by weight of the sugar surfactant are sprayed in the presence of mixtures of soda and zeolites. However, this process only gives compounds with a low surfactant concentration and an inadequate bulk density. Finally, International patent application WO 95/14519 (Henkel) reports on the drying of sugar surfactant pastes with superheated steam. Unfortunately, this is technically very complicated. In fact, there has not yet been a reliable process which enables high-quality, substantially water-free sugar surfactant powders or granules to be produced, but which does not entail the use of carriers during the drying process. Another problem of known processes is that they do not lead to the particularly preferred heavy powders with a bulk density above 500 g/l and, at the same time, a greatly reduced dust content. However, it is precisely these two parameters which are so important on economical, applicational and safety grounds.

German patent DE-C1 195 34 371 (Henkel) describes a process for the production of sugar surfactant granules in which water-containing pastes of alkyl glucosides or fatty acid-N-alkyl glucamides are dried in a thin layer evaporator. The preparations are highly alkalized (pH=11–12) for antimicrobial stabilization. However, a neutral to slightly acidic pH value is required for cosmetic product formulations. The discontinuous nature of the neutralization step in the paste is very time-consuming and can only be reproduced to a limited extent on account of the considerable buffer effect so that frequent readjustment is necessary. In addition, if the pH falls below the neutral point, the paste foams vigorously with evolution of carbon dioxide. In addition, a subsequent heat treatment during drying leads to a poorly reproducible increase in the pH value so that neutral granules cannot readily be produced by this method.

Accordingly, the complex problem addressed by the present invention was to convert water-containing, alkaline sugar surfactant pastes with minimal outlay on equipment into substantially water-free and dust-free granules with a neutral or slightly acidic pH value which, compared with known products, would be distinguished simultaneously by improved colour quality and storage stability, by a high bulk density and by good flow properties

DESCRIPTION OF THE INVENTION

The present invention relates to a process for the production of neutral sugar surfactant granules, in which water-containing pastes of a) alkyl and/or alkenyl oligoglycosides and/or
b) fatty acid-N-alkyl polyhydroxyalkylamides with a solids content of at least 20% by weight and preferably in the range from 25 to 75% by weight are dried in a horizontally arranged thin-layer evaporator or dryer with rotating internals to a residual water content below 2% by weight, preferably below 1.5% by weight and, more preferably, below 1% by weight and, at the same time, converted into particulate form, characterized in that the sugar surfactant pastes are neutralized immediately before entering the thin-layer evaporator/dryer.

It has surprisingly been found that the introduction of the neutralizing agent immediately before the alkaline pastes enter the thin-layer evaporator/dryer leads to rapid and uniform neutralization and ultimately to products which are far more light-colored and color-stable than known products. Conversely, this means that neutralized sugar surfactant pastes can be dried at distinctly higher temperatures, i.e. at increased product throughputs, and that granules equivalent in their color quality to known granules can still be obtained. The products have a high apparent density of 550 to 650 g/l and an average particle diameter of 2 to 4 mm which leads to a reduction in the unwanted absorption of water and in the caking of the particles. High stability in storage is also achieved in this way. At the same time, the particles are dust-free, i.e. the percentage of particles smaller than 200 μm in diameter is less than 5% by weight, and considerably harder than comparable granules which has a favorable effect on their flow properties.

Alkyl and/or alkenyl oligoglycosides

Alkyl and alkenyl oligoglycosides are known nonionic surfactants which correspond to general formula (I):

$$R^1O\text{—}[G]_p \tag{I}$$

where $R^1$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1-0 301 298 and WO 90/03977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, Gurbet alcohols and technical mixtures thereof which may be obtained as described above. Alkyl oligoglucosides based on hydrogenated $C_{12/14}$ coconut oil fatty alcohol having a DP of 1 to 3 are preferred.

Fatty acid-N-alkyl polyhydroxyalkylamides

Fatty acid-N-alkyl polyhydroxyalkylamides are non ionic surfactants corresponding to formula (II):

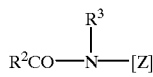

(II)

in which $R^2CO$ is an aliphatic acyl radical containing 6 to 22 carbon atoms, $R^3$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups. The fatty acid-N-alkyl polyhydroxyalkylamides are known compounds which may normally be obtained by reductive amination of a reducing sugar with an alkylamine or an alkanolamine and subsequent acylation with a fatty acid, a fatty acid alkyl ester or a fatty acid chloride. Processes for their production are described in U.S. Pat. Nos. 1,985,424, 2,016,962 and 2,703, 798 and in International patent application WO 92/06984. An overview of this subject by H. Kelkenberg can be found in Tens. Surf. Det. 25, 8 (1988). The fatty acid-N-alkyl polyhydroxyalkylamides are preferably derived from reducing sugars containing 5 or 6 carbon atoms, more particularly from glucose. Accordingly, the preferred fatty acid-N-alkyl polyhydroxyalkylamides are fatty acid-N-alkyl glucamides which correspond to formula (III):

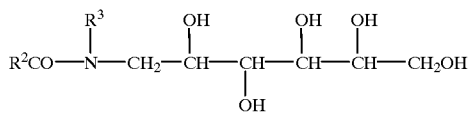

(III)

Preferred fatty acid-N-alkyl polyhydroxyalkylamides are glucamides corresponding to formula (III) in which $R^3$ is an alkyl group and $R^2CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid-N-alkyl glucamides (III) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose.

Neutralization

To neutralize the alkaline sugar surfactant pastes, a continuous stream of an aqueous neutralizing agent is added to the pastes immediately before they enter the thin-layer evaporator/dryer in such a quantity and at such a rate that a pH value of 6.8 to 7.5 is spontaneously established. By means of the high-speed rotor of the evaporator, homogenization is achieved in a very short time so that the formation of acidic or alkaline "knots" can be reliably avoided; there is also no unwanted foaming of the mixture. The neutralizing agent can be regulated by pH measurement in the end product. Basically, aqueous mineral acids or organic acids are suitable neutralizing agents. Phosphoric acid, lactic acid and preferably citric acid in the form of aqueous solutions with a solids content of 25 to 50% by weight are preferably used.

Drying and Granulation in the Thin-Layer Evaporator/Dryer

The simultaneous drying and granulation process takes place in a horizontally arranged thin-layer evaporator or dryer with rotating internals of the type marketed, for example, by the VRV company under the name of "Flash Dryer" or by the Vomm company under the name of "Turbo Dryer". In simple terms, the flash dryer is a tube which can be heated to different temperatures over several zones. The paste-form starting material, which is introduced by a pump, is projected onto the heated wall by one or more shafts fitted with paddles or plowshares as rotating internals and is dried on the heated wall in a thin layer typically with the thickness of 1 to 10 mm. According to the invention, it has been found to be of advantage to apply a temperature gradient of 120–170° C. (product entrance) to 20° C. (product exit) to the thin layer evaporator. To this end, the first two zones of the evaporator for example may be heated to 120–190° C. and preferably to 120–130° C. and the last zone to 20° C. Higher drying temperatures have not been found to be of advantage in view of the thermal lability of the starting materials. The thin-layer evaporator is operated at atmospheric pressure. Air or, for example, an alkaline gas stream is passed through in countercurrent (throughput about 50–150 m$^3$/h for an area of 0.5 m$^2$). The gas entry temperature is generally in the range from 20 to 30° C. while the exit temperature is in the range from 90 to 1 10° C.

The water-containing sugar surfactant pastes which may be used as starting materials may have a solids content above 20% by weight and preferably in the range from 25 to 75% by weight. Typically, their solids content is of the order of 30 to 50% by weight. The throughput is of course dependent on the size of the dryer, but is typically in the range from 5 to 15 kg/h. It is advisable to heat the pastes to 40 to 60° C. during their introduction. In addition, in one preferred embodiment of the invention, the product may even be partly recycled, i.e. part of the product output may be returned to the drying stage and mixed with the aqueous paste.

In addition, after drying, it has proved to be of considerable advantage to transfer the granules, which still have a temperature of around 50 to 70° C., to a conveyor belt, preferably in the form of a vibrating shaft, and rapidly to cool them thereon, i.e. over a period of 20 to 60 seconds, to temperatures of around 30 to 40° C. using ambient air. In order further to improve their resistance to the unwanted absorption of water, the granules may also be "dusted", for example by addition of 0.5 to 2% by weight of silica, alkalil metal carbonate or the like.

Commercial Applications

The granules obtainable by the process according to the invention may be subsequently mixed with other ingredients of powder-form surface-active formulations, for example tower powders for detergents. In addition, the powders may readily be incorporated in aqueous preparations. In fact, where the powders are used, no differences in performance properties are observed in relation to the water-containing starting pastes. The granules may also readily be incorporated in syndet soap formulations and toothpastes, for example together with fatty acids, fatty acid salts, starch, polyglycol and the like.

EXAMPLE

Example 1

The granules were produced in a Flash Dryer of the type manufactured by VRV S.p.A., Milan, Italy. This is a horizontally arranged thin-layer dryer (length 1100 mm, internal diameter 155 mm) with four shafts and 22 paddles of which the distance from the wall is 2 mm. The dryer had three separate heating and cooling zones and a total heat exchange area of, in all, 0.44 m². The dryer was operated at normal pressure. An aqueous paste—heated to 50° C.—of a cocoalkyl oligoglucoside (Plantaren® APG 1200, solids content around 50% by weight) was pumped into the thin-layer dryer by a vibrating pump at a throughput of 11.5 kg/h together with a 30% by weight citric acid solution in a quantity sufficient for neutralization. Peripheral heating zones 1 and 2 of the thin-layer dryer had been adjusted to 185° C. while its cooling zone 3 had been adjusted to 20° C. The rotor speed was 24 m/s. Air was passed through the Flash Dryer at a rate of around 110 m³/h. The gas exit temperature was around 65° C. The predried granules which still had a temperature of around 60° C. were transferred to a vibrating chute (length 1 m), exposed to ambient air and cooled to around 40° C. in 30 s. The granules were then dusted with around 1% by weight of silica powder (Sipernat® 50 S). The characteristic data of the granules are set out in Table 1:

Example 2

Example 1 was repeated except that drying in zones 1 and 2 was carried out at temperatures of 125° C.

Comparison Example C1

Example 1 was repeated except that the paste was not neutralized. The results are set out in Table 1.

TABLE 1

Characteristic data of the Flash Dryer granules (percentages = % by weight)

| Parameter | 1 | 2 | C1 |
|---|---|---|---|
| pH of the product | 7.1 | 7.1 | 11.1 |
| Bulk density [g/l] | 610 | 612 | 612 |
| Residual water content [%] | 0.2 | 0.2 | 0.2 |
| Product color [% reflectance] | 75.3 | 81.2 | 67.5 |
| Particle size distribution [%] | | | |
| >3.15 mm | 38.8 | 38.4 | 39.4 |
| >1.6 mm | 25.7 | 35.3 | 33.3 |
| >0.8 mm | 15.2 | 13.4 | 12.4 |
| >0.4 mm | 9.8 | 8.3 | 7.3 |
| >0.2 mm | 6.4 | 2.3 | 4.5 |
| >0.1 mm | 3.3 | 1.6 | 2.3 |
| <0.1 mm | 0.8 | 0.7 | 0.8 |

What is claimed is:

1. A process for making neutral sugar surfactant granules comprising:

(a) providing a water-containing alkaline sugar surfactant selected from the group consisting of an alkyl oligoglycoside, an alkenyl oligoglycoside, a fatty acid-N-alkyl polyhydroxyalkylamide, and mixtures thereof;

(b) providing a thin-layer evaporator or dryer having rotating internals;

(c) neutralizing the water-containing alkaline sugar surfactant to a pH of from 6.8 to 7.5 to form a neutralized water-containing sugar surfactant;;

(d) introducing the neutralized water-containing alkaline sugar surfactant into the thin-layer evaporator or dryer; and (e) drying the water-containing alkaline sugar surfactant in the thin-layer evaporator or dryer until it has a residual water content below 2% by weight.

2. The process of claim 1 wherein the water-containing alkaline sugar surfactant has a solids content of at least 20% by weight.

3. The process of claim 1 wherein the alkyl and alkenyl oligoglycoside corresponds to formula (I):

wherein $R^1$ is an alkyl and/or alkenyl radical having from 4 to 22 carbon atoms, G is a sugar unit having 5 or 6 carbon atoms, and p is a number from 1 to 10.

4. The process of claim 1 wherein the fatty acid-N-alkyl polyhydroxyalkylamide corresponds to formula (II):

wherein $R_2CO$ is an aliphatic acyl radical having from 6 to 22 carbon atoms, $R^3$ is hydrogen, an alkyl or hydroxyalkyl radical having from 1 to 4 carbon atoms, and [Z] is a linear or branched polyhydroxyalkyl radical having from 3 to 12 carbon atoms and from 3 to 10 hydroxyl groups.

5. The process of claim 1 wherein the thin-layer evaporator or dryer has a temperature gradient of from 190° C. at a product entrance of the evaporator or dryer to 20° C. at a product exit of the evaporator or dryer.

6. The process of claim 1 wherein the granules exiting the thin-layer evaporator or dryer are cooled with ambient air to form cooled granules.

7. The process of claim 6 wherein the cooled granules are then dusted with a powder.

8. The process of claim 1 wherein the water-containing alkaline sugar surfactant has a solids content of from 25 to 75% by weight.

9. The process of claim 1 wherein the granules have an apparent density of from 550 to 650 g/l.

10. The process of claim 1 wherein the granules have an average particle diameter of from 2 to 4 mm.

11. The process of claim 1 wherein the granules are dust free.

* * * * *